US010060866B2

(12) United States Patent
Gellert et al.

(10) Patent No.: US 10,060,866 B2
(45) Date of Patent: Aug. 28, 2018

(54) THERMAL CONDUCTIVITY DETECTOR AND DETECTOR MODULE

(71) Applicant: Siemens Aktiengesellschaft, Munich (DE)

(72) Inventors: Udo Gellert, Bellheim (DE); Glen Eugene Schmidt, Bartlesville, OK (US)

(73) Assignee: Siemens Aktiengesellschaft, Munich (DE)

( * ) Notice: Subject to any disclaimer, the term of this patent is extended or adjusted under 35 U.S.C. 154(b) by 67 days.

(21) Appl. No.: 15/157,710

(22) Filed: May 18, 2016

(65) Prior Publication Data
US 2016/0341681 A1 Nov. 24, 2016

(30) Foreign Application Priority Data
May 20, 2015 (EP) ..................................... 15168393

(51) Int. Cl.
*G01N 30/30* (2006.01)
*G01N 30/66* (2006.01)
(Continued)

(52) U.S. Cl.
CPC ............ *G01N 25/18* (2013.01); *G01N 30/30* (2013.01); *G01N 30/66* (2013.01);
(Continued)

(58) Field of Classification Search
CPC .. G01N 30/66; G01N 30/02; G01N 2030/035; G01N 25/18
(Continued)

(56) References Cited

U.S. PATENT DOCUMENTS

| 3,733,463 A | 5/1973 | Low et al. |
| 4,080,821 A | 3/1978 | Johnston |

(Continued)

FOREIGN PATENT DOCUMENTS

| CN | 102667465 | 9/2012 |
| CN | 103299178 | 9/2013 |

(Continued)

OTHER PUBLICATIONS

Wayne Storr: "Resistor Power Rating"; Electronics Tutorials; XP002750965; gefunden im Internet: URL:https://web.archive.org/web/20150509175038/http://www.electronics-tutorials.ws/resistor/res_7.html; 2015.
(Continued)

*Primary Examiner* — Manish S Shah
*Assistant Examiner* — Jean Morello
(74) *Attorney, Agent, or Firm* — Cozen O'Connor

(57) ABSTRACT

A thermal conductivity detector for a gas chromatograph includes a heatable resistive detector element configured to be physically arranged in a flow of analytes eluting from a chromatography column and electrically arranged together with resistors in separate arms of a measuring bridge, wherein to provide a new configuration of the thermal conductivity detector to allow high detector sensitivity and to meet intrinsic safety requirements, the detector element includes at least two equal detector sub-elements that are configured to be physically arranged in series in the flow of analytes and electrically arranged in parallel with each other, where the detector element in one arm and a reference resistor in the other arm of the same half of the measuring bridge are configured such that the total resistance of the parallel detector sub-elements at operating temperature is at least approximately equal to the resistance of the reference resistor.

8 Claims, 1 Drawing Sheet

(51) Int. Cl.
*G01N 25/18* (2006.01)
*G01N 30/60* (2006.01)
*G01N 30/02* (2006.01)

(52) U.S. Cl.
CPC ... *G01N 30/6095* (2013.01); *G01N 2030/025* (2013.01); *G01N 2030/3053* (2013.01)

(58) Field of Classification Search
USPC .................................................. 73/23.25
See application file for complete search history.

(56) References Cited

U.S. PATENT DOCUMENTS

| | | |
|---|---|---|
| 5,587,520 A | 12/1996 | Rhodes |
| 5,756,878 A | 5/1998 | Muto et al. |
| 2008/0291966 A1 | 12/2008 | Engel et al. |
| 2013/0133403 A1 | 5/2013 | Gellert et al. |
| 2013/0241416 A1 | 9/2013 | Toth |
| 2014/0157866 A1 | 6/2014 | Probst et al. |

FOREIGN PATENT DOCUMENTS

| | | |
|---|---|---|
| CN | 203606335 U | 5/2014 |
| EP | 0 724 151 | 7/1996 |
| WO | WO 2009/095494 | 8/2009 |
| WO | WO 2012/044169 | 4/2012 |

OTHER PUBLICATIONS

Cruz et al.: "Microfabricated thermal conductivity detector for the micro-ChemLab (TM)"; Sensors and actuators B: Chemical: International Journal Devoted to Research and Development of Physical and Chemical Transducers, Elsevier S.A. vol. 121, No. 2, pp. 414-422: XP005872220; ISSN: 0925-4005, DOI:10.1016/J.SNB.2006.04.107; 2007.

THERMAL CONDUCTIVITY DETECTOR AND DETECTOR MODULE

BACKGROUND OF THE INVENTION

1. Field of the Invention

The present invention relates to a thermal conductivity detector module and a thermal conductivity detector for a gas chromatograph comprising a heatable resistive detector element configured to be physically arranged in a flow of analytes eluting from a chromatography column and electrically arranged together with resistors in separate arms of a measuring bridge, where the detector element comprises at least two equal detector sub-elements that are configured to be physically arranged in series in the flow of the analytes and electrically arranged in parallel with each other.

2. Description of the Related Art

A thermal conductivity detector of the above mentioned type is known from U.S. Pat. No. 4,080,821 discloses a thermal detector to be used, inter alia, as a flow meter or as a thermal conductivity detector for, e.g., a gas chromatograph. In order to make the detector substantially independent of ambient temperature, the detector has a detector element with three detector sub-elements that have closely matched resistance values and that are arranged in series in the flow of a gas to be measured. Two of the detector sub-elements are electrically arranged in parallel with each other in one arm and the third one in the other arm of the same half of a measuring bridge. An amplifier detects a differential voltage between the connecting nodes of the arms of the respective halves of the measuring bridge and applies an output voltage to the connecting nodes of the halves of the measuring bridge in order to maintain the bridge substantially in balance. This causes heating of the three detector sub-elements, where the heating effect in the third detector sub-element is four times that in the parallel detector sub-elements. If the known thermal detector is used as a thermal conductivity detector, an additional resistor is provided in series with the parallel connected detector sub-elements.

Thermal conductivity detectors are used to detect certain liquid or gaseous substances (fluids) based their characteristic thermal conductivity, particularly in gas chromatography. There, components or substances of a gas mixture are separated by passing a sample of the gas mixture in a carrier gas (mobile phase) through a separation column containing a stationary phase. The different components interact with the stationary phase, which causes each component to elute at a different time that is known as the retention time of the component. The separated substances, also referred to as analytes, are detected by a thermal conductivity detector that has a measuring cell with an appropriate detector element, e.g., an electrically heated filament disposed in a measurement channel. Depending on the thermal conductivity of the analyte flowing past the heated filament, more or less heat is diverted from the heating filament to the wall of the measurement channel, and the heating filament is correspondingly cooled to a greater or lesser degree. As a result of the cooling of the heating filament, its electrical resistance changes, which is detected.

For this purpose and as known from, e.g., U.S. Pat. No. 5,756,878, the heating filament and additional resistors may be disposed in different arms of a measuring bridge. The thermal conductivity of the substance passing the heating filament is obtained from an amount of energy that is supplied to the measuring bridge and is controlled to maintain the temperature of the heating filament at a predetermined temperature. To this end, an operational amplifier detects a differential voltage between the connecting nodes of the arms of the respective halves of the measuring bridge and applies an output voltage to the connecting nodes of the halves of the bridge.

The sensitivity of the detector depends on several factors. Generally, it will be higher, the higher the temperature between the detector element and the wall of the measurement channel is and the higher the resistance of the detector element is. Filaments of metal, in particular gold, have been used for a long time. In order to get a sufficiently high resistance, the filament must be made very thin which, however, leads to poor robustness. Moreover, gases containing hydrogen sulfide can destroy the gold filament. Platinum has some advantages over gold but shows a catalytic effect in gas mixtures that contain hydrogen and hydrocarbons.

A thermal conductivity detector is known from WO 2009/095494 A1, where the electrically heatable filament is micro-machined from doped silicon to achieve a long service life and inertness toward chemically corrosive gas mixtures. Due to its much higher melting point, the silicon filament can operate at a higher temperature than a gold filament. Furthermore, the specific resistance of silicon is higher than that of gold, so that high detection sensitivity is achieved.

A high resistance of the detector element, however, proves to be detrimental if the thermal conductivity detector has to be intrinsically safe. Intrinsic safety (IS) relies on equipment designed so that it is unable to release sufficient energy, by either thermal or electrical means, to cause an ignition of a flammable gas. Thus, intrinsic safety can be achieved by limiting the amount of power available to the electrical equipment in a hazardous area to a level below that which will ignite the gases. There are various IS standards set forth by various certifying agencies for a system to be considered intrinsically safe. Such standards include International Electrical Commission (IEC) IEC 60079-11, Factory Mutual (FM) 3610, Underwriters Laboratories (UL) UL913, Canadian Standards Association CAN/CSA-C22.2 No. 157-92, etc.

The detector element requires a certain electrical power to be heated to and stabilized at the wanted operating temperature. The higher the operating resistance, the higher the voltage across the detector element ($P=V^2/R$, where P, V and R denote the power, voltage and resistance, respectively). The sensitivity of the measuring bridge is maximum if the operating resistance of the detector element and the resistance of a reference resistor in the other arm of the same half of the measuring bridge are equal. The voltage which drives the bridge is then twice the voltage across the detector element. In case of a short circuit of the detector element, the short-circuit current will be limited by the reference resistor and will be twice the operating current through the detector element. Table A.1 of the above mentioned IEC standard, for example, denotes the permitted short-circuit current corresponding to the voltage, where the permitted current decreases highly disproportionately with the voltage increasing. Thus, in view of the relatively high voltage required to drive the bridge with the high-resistance detector element, the reference resistor might not be able to limit the short-circuit current to the permitted value.

This applies in particular, if the thermal conductivity detector is one of a plurality of detectors that are integrated on a thermal conductivity detector module, which module as a whole shall be intrinsically safe. In this case, the individual detectors cannot be treated as separate intrinsically safe devices unless separated by 6 mm through the entire electrical path. Such separation, however, is not feasible when all detectors must be close together as known from modules with four detectors typically used in gas chromatographs. Consequently, the sum of the short-circuit currents of all integrated detectors may not exceed the permitted value.

An approach to solve the problem would be to lower the resistance of the reference, which facilitates a lower voltage to drive the measuring bridge. This would, however, also allow for a greater short-circuit current, thus still violating the IS parameters. Moreover, for the reasons given above, the sensitivity of the measuring bridge would be compromised.

SUMMARY OF THE INVENTION

It is therefore an object of the present invention to provide a new configuration for a thermal conductivity detector that allows for both high detector sensitivity and allows intrinsic safety requirements to be met.

These and other objects and advantages are achieved in accordance with the invention by providing a thermal conductivity detector in which the detector element in one arm and a reference resistor in the other arm of the same half of the measuring bridge are configured such that the total resistance of the parallel detector sub-elements is at least approximately equal to the resistance of the reference resistor at operating temperature.

In accordance with the invention, a thermal conductivity detector for a gas chromatograph comprises a heatable resistive detector element configured to be physically arranged in a flow of analytes eluting from a chromatography column and electrically arranged together with resistors in separate arms of a measuring bridge, where the detector element comprises at least two equal detector sub-elements that are configured to be physically arranged in series in the flow of the analytes and electrically arranged in parallel with each other, and where the detector element in one arm and a reference resistor in the other arm of the same half of the measuring bridge are configured such that the total resistance of the parallel detector sub-elements is at least approximately equal to the resistance of the reference resistor at operating temperature.

The approach of the invention is to divide a single prior art detector element with a resistance R into n parallel sub-elements each having a resistance R/n. Thus the overall electrical resistance of detector element will be reduced to R/n2. From a fluidic point of view, however, the detector element remains practically unchanged because the detector sub-elements are serially arranged in the flow of the analytes. As the operation temperature of the detector element shall remain unchanged, the power necessary will also remain unchanged. Thus, given a constant power P, the voltage U across the detector element will be lower, namely U=1/n·(P·R)1/2. As mentioned above, the maximum permissible current depends on the voltage, the current decreasing highly disproportionately with the voltage increasing. More precisely and as can be seen from the Table A.1 of the IEC standard, the product of the voltage and the corresponding permissible current decreases as the voltage increases. Therefore, the detector element segmented into two or more parallel sub-elements allows for a higher power and operating temperature than the single prior art detector element without violating the intrinsic safety requirements, while the sensitivity of the measuring bridge is maximum. This, in turn, implies that a thermal conductivity detector with a high-resistance detector can be made intrinsically safe by segmenting the detector element.

In an embodiment of the invention, the detector element is a MEMS-device, preferably made of micro-machined silicon.

In a further embodiment of the invention, the heatable resistive detector element comprises three detector sub-elements.

Thus, as an example, a prior art silicon-based detector element in the order of, e.g., 15 kΩ can be segmented into three detector sub-elements of 5 kΩ, respectively. This will not only permit the design of the thermal conductivity detector or at least the half of the measuring bridge containing the detector element to meet an intrinsic safety requirement but also to provide an intrinsically safe thermal conductivity detector module comprising at least two, preferably four, thermal conductivity detectors.

In order to maintain the temperature of the detector element at a predetermined operating temperature, the thermal conductivity detector preferably comprises an amplifier that detects a differential voltage between the connecting nodes of the arms of the respective halves of the measuring bridge and applies an output voltage to the connecting nodes of the halves of the measuring bridge.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will now be described by way of example and with reference to the accompanying drawing, in which.

DETAILED DESCRIPTION OF THE EXEMPLARY EMBODIMENTS

Figure 1:
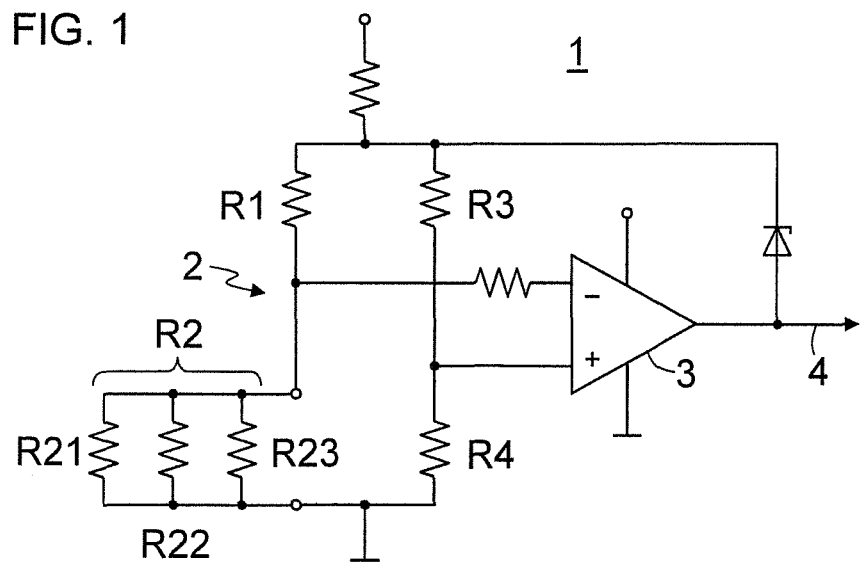
FIG. 1 is an exemplary schematic diagram of the thermal conductivity detector in accordance with an embodiment of the invention.

FIG. 1 illustrates a thermal conductivity detector 1. A reference resistor R1 and a detector element R2 are arranged in one half of a measuring bridge (Wheatstone bridge) 2, and further resistors R3 and R4 are arranged in the other half. The measuring bridge 2, i.e., each of its halves, is excited by the output of a difference amplifier 3 that drives a voltage through the reference resistor R1 and onto the detector element R2 in order to control its resistance and, thus, its temperature. A voltage at the node between the reference resistor R1 and the detector element R2 is applied to either one of the inverting and non-inverting input of the amplifier 3, and a voltage at the node between the resistors R3 and R4 is applied to the other input of the amplifier 3.

In the example shown, the difference amplifier 3 is configured for a detector element having a positive temperature coefficient (PTC) of resistance. In the case of a negative temperature coefficient (NTC) detector element, the inputs of the difference amplifier 3 have to be swapped.

The difference amplifier 3 controls the current supplied to the detector element R2 such that the voltage generated at the connection point between the reference resistor R1 and the detector element R2 becomes equal to the voltage generated at the connection point between the resistors R3 and R4, thereby keeping the resistance value of the detector element R2 constant so that R1/R2=R3/R4. As a result, the output voltage signal 4 of the detector 1 is a measure of the voltage required to keep the detector element R2 at a certain operating temperature, and thus at a certain reference resistance, as a gaseous component that is mixed with a carrier gas flows across the detector element R2. The resistance of the reference resistor R1 is chosen to be equal to the operating resistance of the detector element R2 so that the sensitivity of the measuring bridge 2 is maximum. Consequently, the voltage that drives the measuring bridge 2 is twice the respective voltages across the reference resistor R1 and the detector element R2. In case of a short circuit of the detector element R2, the short-circuit current will be limited by the reference resistor R1 and will be twice the operating current through the detector element R2. The resistance values of the resistors R3 and R4 are much higher than those of R1 and R2 but have the same ratio.

The ratio of R1 to R2 may deviate from 1:1 in order to allow for a lower power supply voltage to the measuring bridge 2 (R2>R1) or a lower short-circuit current (R1>R2).

The detector element R2 is segmented into at least two, here three, equal detector sub-elements R21, R22, R23 that are electrically arranged in parallel with each other. If R is the resistance of each individual sub-elements the total resistance of the three sub-elements R21, R22, R23 is R2=R/3.

Figure 2:
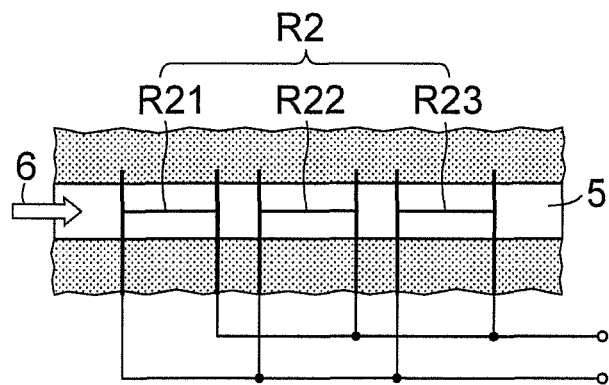
FIG. 2 is an exemplary illustration of an arrangement of several detector sub-elements in a measurement channel.

FIG. 2 schematically illustrates a measurement channel 5 in which the detector sub-elements R21, R22, R23 are arranged in series in a flow 6 of analytes eluting from a chromatography column (not shown). The chromatographically separated analytes pass the detector sub-elements R21, R22, R23 that are in the form of heating filaments. Here, the detector element R2 is a MEMS-device made of micromachined silicon. The detector sub-elements R21, R22, R23 replace a prior art filament of the same over-all length and with a resistance of 3 R. Thus the total resistance of the detector element R2 is one-ninth of the resistance of a prior art filament.

Figure 3:
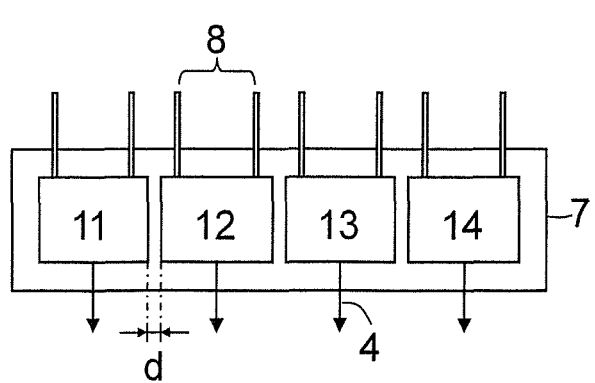
FIG. 3 is an exemplary schematic block diagram of a thermal conductivity detector module in accordance with an embodiment of the invention.

FIG. 3 is an illustration of an exemplary embodiment of a thermal conductivity detector module 7 that comprises four thermal conductivity detectors 11, 12, 13, 14 identical with that of the embodiment of FIGS. 1 and 2. The conductivity detectors 11, 12, 13, 14 not just individually but together meet intrinsic safety requirements. This means that the short-circuit current of each conductivity detector 11, 12, 13, 14 is one-fourth or less the maximum permissible current of an intrinsically safe device on its own. Therefore, the individual detectors do not need to be treated as separate intrinsically safe devices and can be arranged very close together with a gap d of far less than 6 mm. Reference number 8 denotes fluid connectors of the conductivity detectors 11, 12, 13, 14.

While there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A thermal conductivity detector for a gas chromatograph comprising: a measuring bridge having separate arms; and a heatable resistive detector element configured to be physically arranged in a flow of analytes eluting from a chromatography column and electrically arranged together with resistors in separate arms of the measuring bridge; wherein the heatable resistive detector element comprises at least two equal detector sub-elements which are configured to be physically arranged in series in the flow of the analytes and electrically arranged in parallel with each other; and wherein further the heatable resistive detector element in one arm and a reference resistor in another arm of the same half of the measuring bridge are configured such that a total resistance of the parallel at least two equal detector sub-elements is at least substantially equal to a resistance of the reference resistor at operating temperature.

2. The thermal conductivity detector of claim 1, wherein the heatable resistive detector element comprises three detector sub-elements.

3. The thermal conductivity detector of claim 1, wherein the heatable resistive detector element is a silicon-based micro-machined element.

4. The thermal conductivity detector of claim 2, wherein the heatable resistive detector element is a silicon-based micro-machined element.

5. The thermal conductivity detector of claim 1, further comprising: an amplifier configured to detect a differential voltage between connecting nodes of arms of respective halves of the measuring bridge and further configured to apply an output voltage to the connecting nodes of the halves of the measuring bridge in order to maintain the detector sub-elements at the operating temperature.

6. The thermal conductivity detector of claim 1, wherein at least a half of the measuring bridge containing the detector element is configured to meet an intrinsic safety requirement.

7. A thermal conductivity detector module comprising at least two thermal conductivity detectors in accordance with claim 1.

8. The thermal conductivity detector module of claim 7, wherein four of said thermal conductivity detectors 7 are provided.

* * * * *